United States Patent [19]

Malay et al.

[11] Patent Number: 5,415,648

[45] Date of Patent: May 16, 1995

[54] MULTIPLE PURPOSE SYRINGE

[76] Inventors: Manuel R. Malay, 627 Salem La., Brunswick, Ohio 44212; Wilfredo M. Paras, 8501 Oakwood La., North Royalton, Ohio 44133; Eulogio R. Sioson, 25310 S. Woodland, Beachwood, Ohio 44122

[21] Appl. No.: 88,806

[22] Filed: Jul. 8, 1993

[51] Int. Cl.⁶ .................................................. A61M 5/00
[52] U.S. Cl. .................................. 604/181; 604/196; 604/110
[58] Field of Search .............. 604/181, 198, 187, 110, 604/192, 194, 195, 196, 197, 89, 232, 236, 240; 128/919

[56] References Cited

U.S. PATENT DOCUMENTS

| | | |
|---|---|---|
| 4,976,701 | 12/1990 | Ejlersen et al. |
| 4,976,702 | 12/1990 | Andrews et al. ................... 604/198 |
| 5,069,225 | 12/1991 | Okamura ............................ 604/187 |
| 5,114,405 | 5/1992 | Winter ................................. 604/110 |
| 5,120,311 | 6/1992 | Sagstetter et al. ................. 604/187 |
| 5,122,117 | 6/1992 | Haber et al. |
| 5,122,118 | 6/1992 | Haber et al. ........................ 604/110 |
| 5,125,899 | 6/1992 | Frignoli ............................... 604/110 |
| 5,125,908 | 6/1992 | Cohen ................................. 604/196 |
| 5,354,287 | 10/1994 | Wacks ................................. 604/232 |

FOREIGN PATENT DOCUMENTS

| | | | |
|---|---|---|---|
| 8400011 | 1/1984 | WIPO | 604/187 |
| 9218186 | 10/1992 | WIPO | 604/195 |

*Primary Examiner*—C. Fred Rosenbaum
*Assistant Examiner*—V. Alexander

[57] ABSTRACT

A syringe comprising an outer tube for housing a needle/needle gasket assembly, an inner tube closed at one end by a gasket which cooperated with the needle gasket assembly for advancing and projecting the needle out of the outer tube and retracting the needle into the outer assembly when finished, and wherein the inner tube can function as a container for transporting any fluid drawn into the inner tube. The syringe can also be adapted for multiple extractions of fluid using an evacuation collection tube.

19 Claims, 7 Drawing Sheets

MULTIPLE PURPOSE SYRINGE

FIELD OF THE INVENTION

The invention relates to a disposable syringe, and more preferably to a syringe that can only be used once, thereby creating a new type of safety syringe.

BACKGROUND OF THE INVENTION

The need to prevent re-use of syringes is widely recognized in the medical field since unnecessary exposure to acquired immune deficiency syndrome (AIDS) and hepatitis continues to be a problem. In addition, industrial workers who use syringes filled with dangerous fluids in their work are susceptible to be stuck with an exposed needle. The most common procedure done in hospitals or medical offices is to give an injection and withdraw blood or other body fluids from a patient. Syringes are generally used for this purpose. One of the drawbacks of the current procedure is that after use the needle has to be recapped. The majority of reported cases of occupational exposure to contamination or hazardous fluids is due to needle sticks. Therefore, needle sticks are a cause of transmission of diseases to medical and industrial workers. Needle sticks occur not only on failure to recap needles but also during the process of recapping needles.

U.S. Pat. No. 5,120,311 discloses an insert for supporting a double ended needle during a blood collection procedure which is translatable mounted within a cylinder for retracting the anterior needle into the cylinder on completion of the procedure to prevent needle stick while the posterior needle remains continually shielded against needle stick by the insert. An anterior lock position stabilizes the double ended needle during the blood collection procedure and a posterior lock position retains both ends of the needle shielded. A ramp may be associated with the posterior lock position to prevent further translation of the insert and reuse of the holder. For a reusable holder embodiment, the used double ended needle is retracted, safely enclosed and locked inside the cylinder. The anterior end of the cylinder is adapted for receiving the open end of a conventional needle shield to permit gripping of the needle supporting hub and disengagement of the needle from the insert without exposure to needle stick. A replacement needle may then be mounted in the insert and the holder re-used.

U.S. Pat. No. 4,976,702 discloses a shield for a syringe mounted hypodermic needle which utilizes a translucent sheath. The sheath extends over the barrel to one position adjacent the barrel flange and to another position or beyond the needle point. The sheath may be distinctly stopped at these positions.

U.S. Pat. No. 5,114,405 discloses a single use tamper resistant syringe having a locking member which prevents retraction of the plunger after the latter has been fully depressed and discharging the contents of the syringe. The proximal end of the plunger is provided with an abutment and the inside of the barrel is provided with dogs which are biased inwardly. When the plunger is depressed and the abutment slides by the dogs, the latter extend into the barrel to block retraction of the plunger. Tampering of the locking arrangement prior to use of the syringe is prevented by providing a detachable piston cap at the distal end of the plunger so that when the plunger is removed prior to use the cap is dislodged by said dogs and remains within the barrel of the syringe thereby rendering inoperative the syringe.

U.S. Pat. No. 5,069,225 discloses a blood collection and/or injection device includes a double-ended medical needle including a cannula having opposite pointed ends, a hub fitted over the cannula, a rubber sheath optionally fitted over an end portion of the cannula, a cylindrical holder having an opening defined in one end thereof, the end portion of the cannula which is optionally covered with the rubber sheath being adapted to be inserted into the opening with the hub held in the opening by the cylindrical holder, and an evacuated blood collection tube or syringe adapted to be inserted into the cylindrical holder through an opening defined in the opposite end of the cylindrical holder and pierced by the end portion of the cannula. The hub has spreading teeth, and the cylindrical holder includes a holder casing having chuck teeth spreadable radially outwardly by the spreading teeth of the hub. The cylindrical holder also includes a ring having recesses for receiving the spreading teeth, and a cap engaging portion is provided on the ring for receiving a cap thereon.

U.S. Pat. No. 5,122,118 discloses an automatic needle-retracting syringe in which the needle automatically retracts into the barrel of the syringe without the user doing anything. This typically occurs automatically after a predetermined time lapsed from dispensing a liquid injectant from the syringe. Even if the used syringe is simply thrown onto the ground, the needle will automatically be retracted into the barrel after the period of time, such as 30 to 60 seconds, after the injection.

U.S. Pat. No. 5,125,899 discloses a syringe which comprises a shaft having appendix to which a plunger slidable within the syringe cylinder is sealingly connected. At that end at which the hypodermic needle is mounted the cylinder comprises a hole into which a hollow element having a shaped element integral therewith and projecting into the cylinder is inserted and locked. This shaped element becomes securely coupled to a portion shaped complementary to it provided at the adjacent free end of the plunger carried by the shaft to prevent the re-use of the syringe after the shaft has been lowered to firmly engage the shaped portion with the shaped element projecting from the cylinder since withdrawal of the shaft would cause disengagement of the plunger from the shaped appendix of the shaft.

It is an object of the present invention to provide a syringe with a retractable needle.

It is another object of the present invention to provide a syringe with a single use application.

It is another object of the present invention to provide a retractable needle syringe that contains a self contained specimen container.

It is another object of the present invention to provide a tamper proof retractable needle syringe.

It is another object of the present invention to provide a safe holder for any vacuum tube sampling system for multiple extraction of specimen.

It is another object of the present invention to provide a single syringe design which can be used as an injector, extractor and for multiple evacuation.

Other features and advantages of the invention will appear from the following description in which the preferred embodiments have been set forth in detail in conjunction with the accompanying drawings.

SUMMARY OF THE INVENTION

The invention relates to a syringe with a retractable needle comprising an outer tube having a first end and a second end with said first end being opened; a releasable secured first gasket means within said outer tube, said first gasket means securing a needle opened at both ends and protruding from one end of said first gasket means towards the first end of the outer tube and protruding from the opposite end of said gasket means toward the second end of said first gasket means; an inner tube slidably mounted within said outer tube and having a first end and a second end with a second gasket means secured to the first end and said second gasket means adapted to be secured to and release the first gasket means upon contact with the first gasket means so that said first gasket means can be projected toward the second end of the outer tube whereupon said needle can be extended outside the outer tube and when said second gasket means is retracted it will return the first gasket means to its secured position within said outer tube; said second gasket means being aligned with the protruding needle from the first gasket means so that said needle is positioned to extend into the inner tube through said second gasket means prior to said inner tube advancing the first gasket means to the second end of the outer tube; a plunger means positioned within said inner tube having a third gasket means at one end so that when the plunger means is retracted from within said inner tube, the third gasket means will provide a sucking force within said inner tube.

Preferably, the second end of the outer tube is closed and the closure material in alignment with the needle is made of a material that can be easily punctured by the needle when the first gasket means is projected to the second end of the outer tube. In a similar manner, the second gasket means that closes the first end of the inner tube can be formed so that the closure area in alignment with the needle is made of a material that can be easily punctured by the needle when the inner tube is advanced to contact and push the first gasket means to the second end of the outer tube whereupon the needle will be extended from the outer tube and be in a position for use. The second gasket means could be equipped with a locking ring that could lock onto the first gasket means during the projection of the needle outside the outer tube and then upon being retracted, the locking ring would position the first gasket means into its secured position but would be replaced on the second gasket means. After the first gasket means is positioned into its secured position, an addition advancement of the second gasket means with the displaced locking ring would be unsuccessful in advancing the first gasket means to project the needle out of the outer tube. In this embodiment, the syringe could only be used once and therefore would have to be discarded with the needle fully secured within the outer tube. The first and second gaskets could be made of any material such as propylene, polyethylene, and butyl rubber.

In another embodiment of the invention, the third gasket means connected to the end of the plunger could be removed from the inner tube when the fluid in the inner tube has reached a desired amount so that said inner tube could be the container for transporting the fluid. In this embodiment, the opening in the second gasket means created by the needle will have to be sealed by any convention method. For example, the material of the gasket that faces the needle could be a resealable material so that after the needle is withdrawn, the material will seal itself.

For multiple use, such as retraction applications, an evacuation collection tube could be used instead of the plunger member and then when filled, it could be replaced with a second evacuation collection tube. This procedure could be continued for as many tubes of fluid as required.

The syringe of this invention is safe to operate and easy to dispose of after use since the needle will be stored within the outer tube and therefore does not have to be recapped. This will effectively eliminate accidental needle punctures that could lead to the transmittal of communicable disease. The syringe can be safely used as an injector or as an extractor of fluid from any source. In one embodiment, the syringe is designed with a tamper proof means that will permit only one use of the needle and then store the needle within the outer tube so that it can not be used again. The inner tube can be used as a container for the fluid for transporting the fluid to a particular destination. The inner tube can be easily disassembled from the outer tube, if desired, so that only the inner tube with the fluid specimen can be sent to a final destination, such as a testing laboratory.

The above and other objects, features and advantages of the present invention will become more apparent from the following description when taken in conjunction with the accompanying drawings in which preferred embodiments of the present invention are shown by way of illustrative example.

Figure 1:
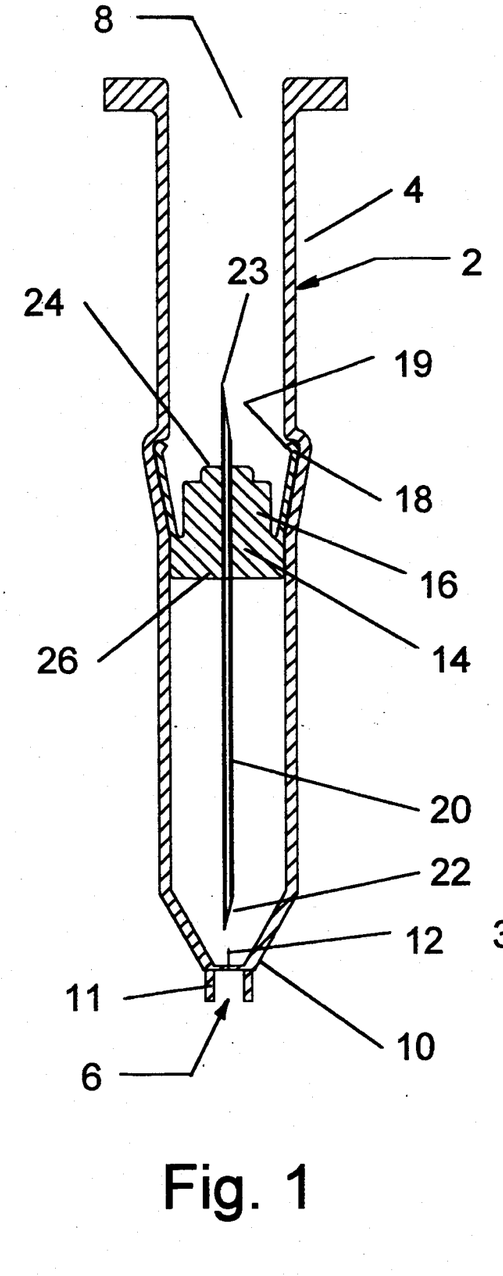
FIG. 1 is a longitudinal cross-sectional view of an outer tube containing a secured needle in accordance with this invention.

Referring to FIG. 1, an outer tube 2 is shown comprising a longitudinal tube 4 closed at one end 6 and open at the other end 8. The closed end 6 terminates with a tapered segment 10 and circular flange 11. A thin membrane segment 12 is provided as a closing for the tube 4. The extended flange provides a recess cavity to accommodate the needle 20 to prevent accidental contact of the needle with a specimen. The recess cavity is also adapted to accommodate a machine port for an Arterial Blood Gas Machine where the specimen could easily be injected and in which the needle tip would protrude only beyond the thin membrane. Releasable secured within tube 4 is a gasket 14 composed of a control core 16 and four spaced apart flexible ribs 18. Ribs 18 are shown secured in groove 19 formed in tube 4. If desired, the four flexible ribs could be replaced with a flexible annular member that could be compressed to the inner diameter of tube 4. Secured in gasket 14 is a hollow needle 20 having open ends 22 and 23. The needle 20 extends above the top surface 24 and below the bottom surface 26 of gasket 14. As shown in FIG. 1, gasket 14 can be projected downward whereupon the ribs will be compressed inwardly and then the open end 22 of needle 20 will pierce closure area 12 and project needle 20 outside of tube 4. The open end 22 needle 20 is cut at a 45° angle to provide a sharper tip for puncturing the closure area 12. The angle of the cut could vary from 30° to 60° with 45° being preferred. If desired, a cap terminal (not shown) with a sharp point could be placed over opening 22 to prevent any foreign material from entering the needle when the needle punctures closure area 12. After the needle projects through the tube 4, the cap terminal could be removed.

Figure 2:
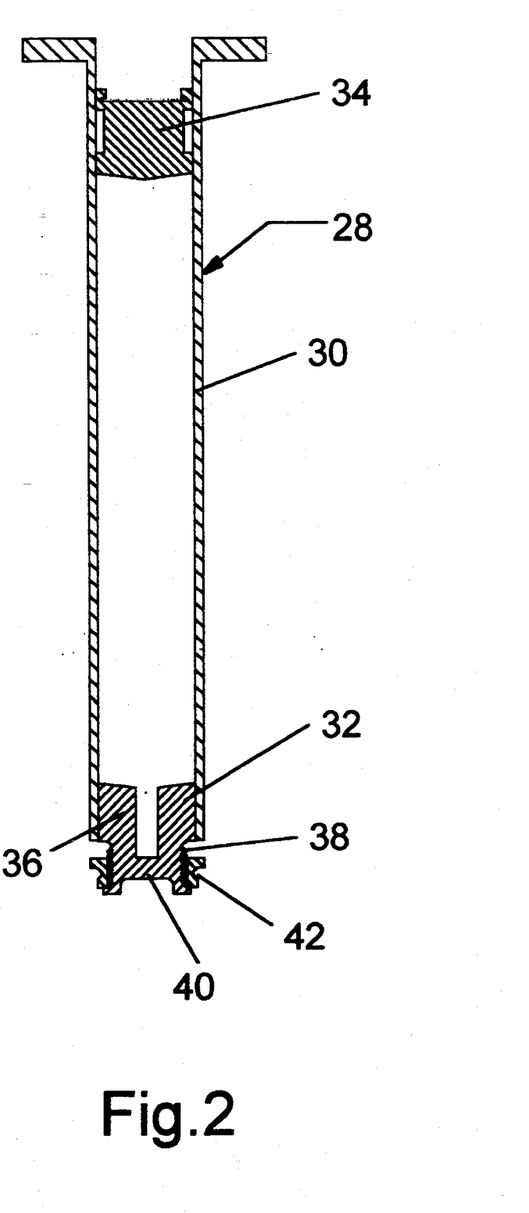
FIG. 2 is a longitudinal cross-sectional view of an inner tube in accordance with this invention.

FIG. 2 shows an inner tube 28 comprising a longitudinal tube 30 closed at one end with a gasket 32 and the other end with a slidable member 34. Gasket 32 comprises a core member 36 secured within the end of tube 28 and providing a groove 38 to accommodate a lock ring 42 disposed at the lower end of groove 38. Core member 36 of gasket 32 shows a thin membrane layer 40 at its central areas.

Figure 3:
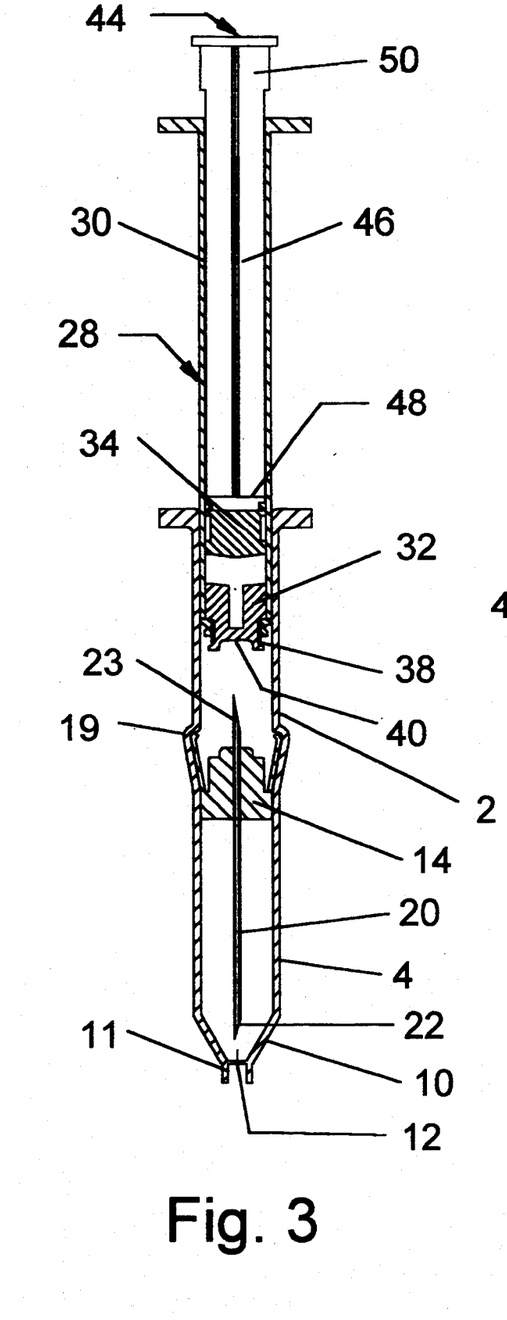
FIG. 3 is a longitudinal cross-sectional view of the syringe of this invention showing the inner tube of FIG. 2 containing a plunger and disposed partially within the outer tube of FIG. 1.
Figure 4:
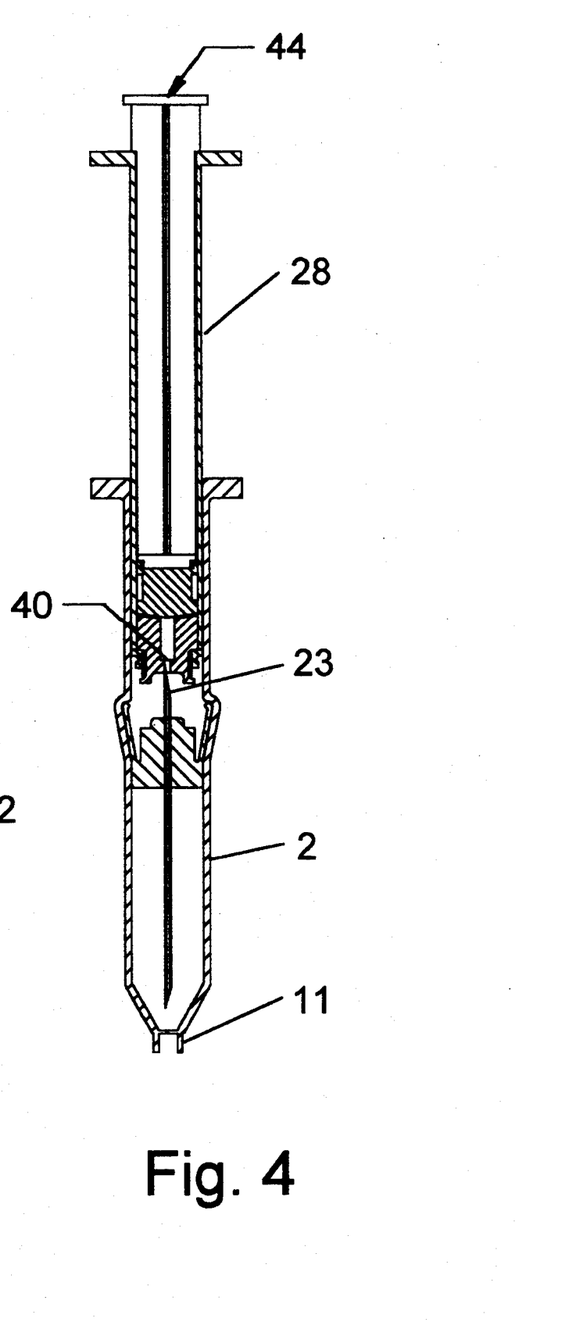
FIG. 4 is a longitudinal cross-sectional view of the syringe of FIG. 3 showing the inner tube partially advanced within the outer tube.
Figure 5:
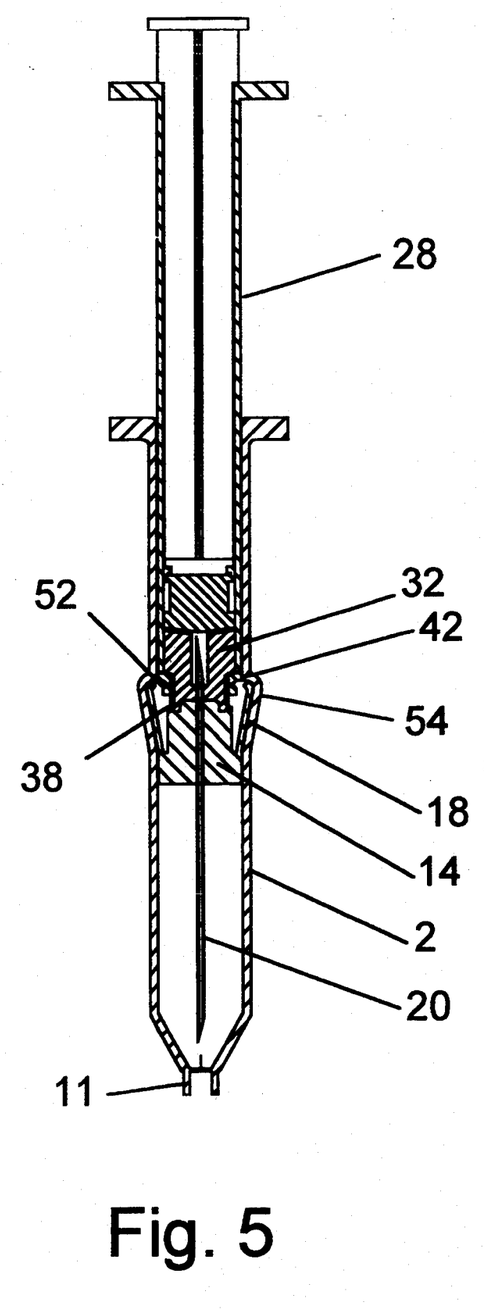
FIG. 5 is a longitudinal cross-sectional view of the syringe of FIG. 4 showing the inner tube further advanced within the outer tube.
Figure 6:
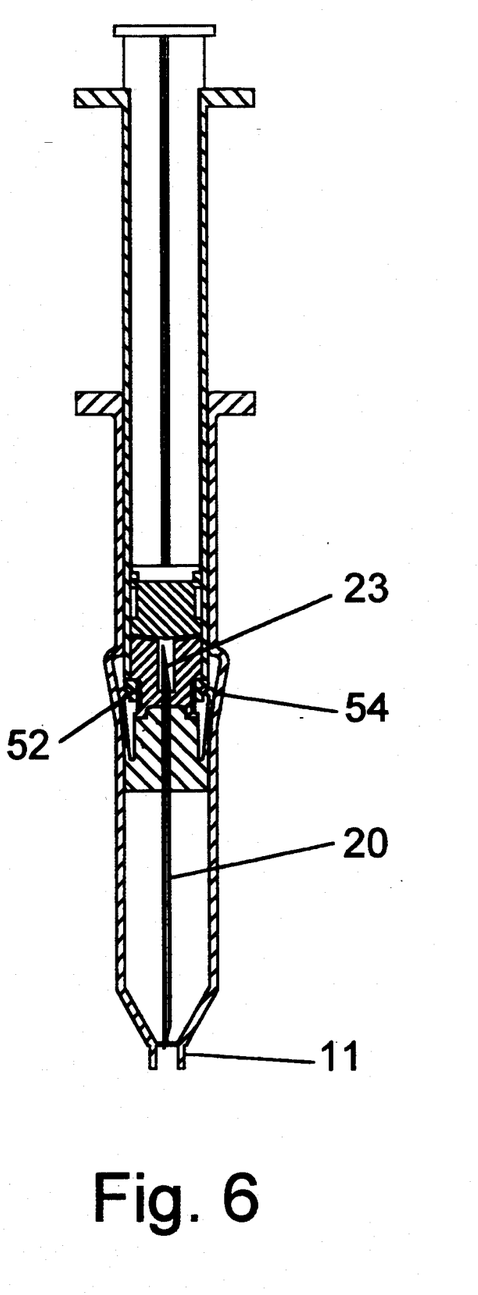
FIG. 6 is a longitudinal cross-sectional view of the syringe of FIG. 5 showing the inner tube further advanced within the outer tube.
Figure 7:
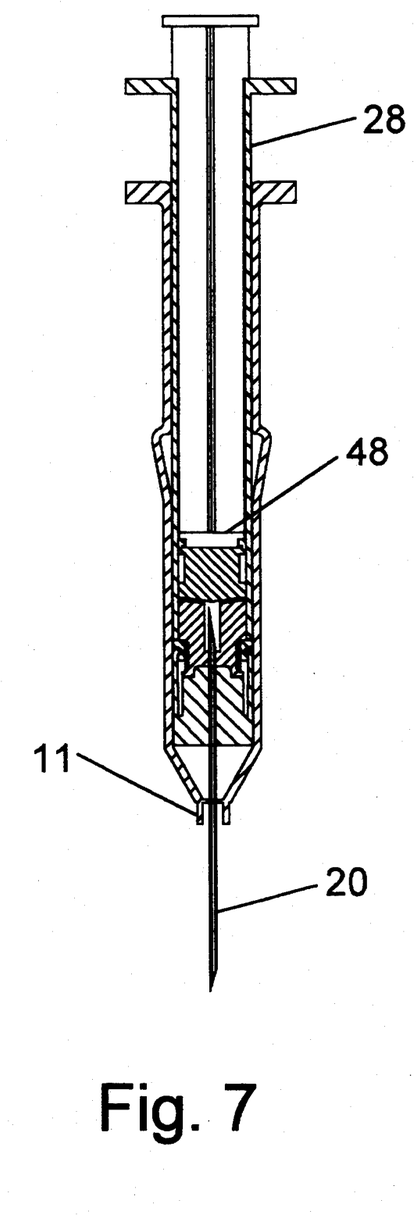
FIG. 7 is a longitudinal cross-sectional view of the syringe of FIG. 6 showing the inner tube of FIG. 6 further advanced within the outer tube.
Figure 8:
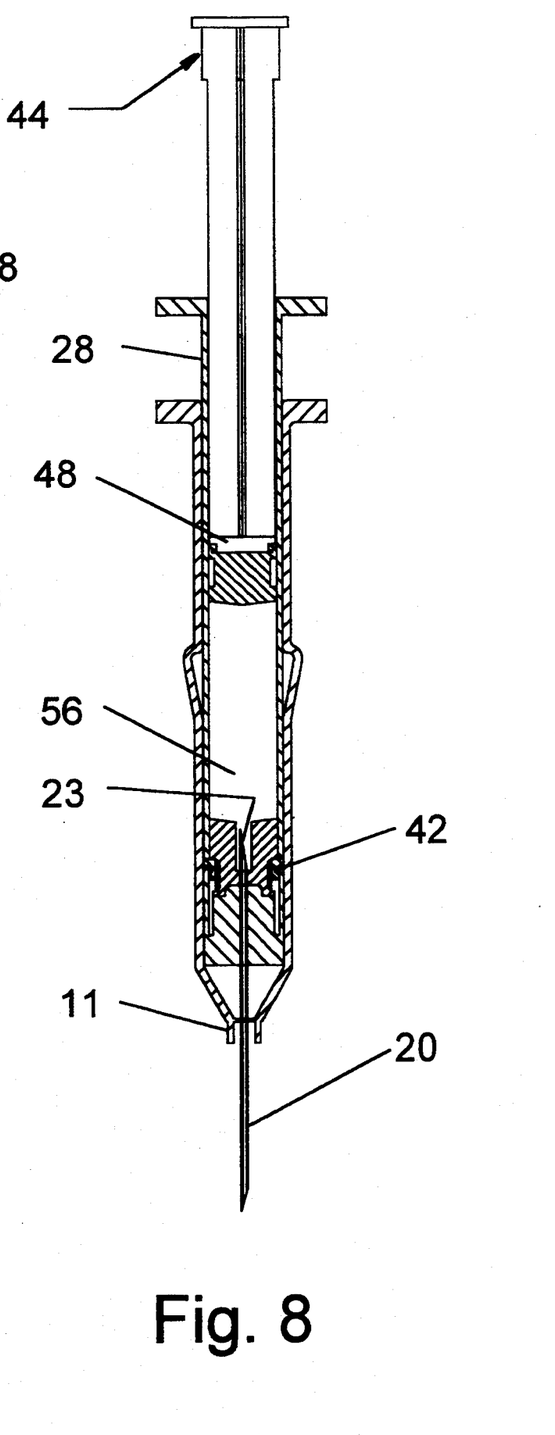
FIG. 8 is a longitudinal cross-sectional view of the syringe of FIG. 7 showing the plunger in the inner tube being retracted from within the inner tube.
Figure 9:
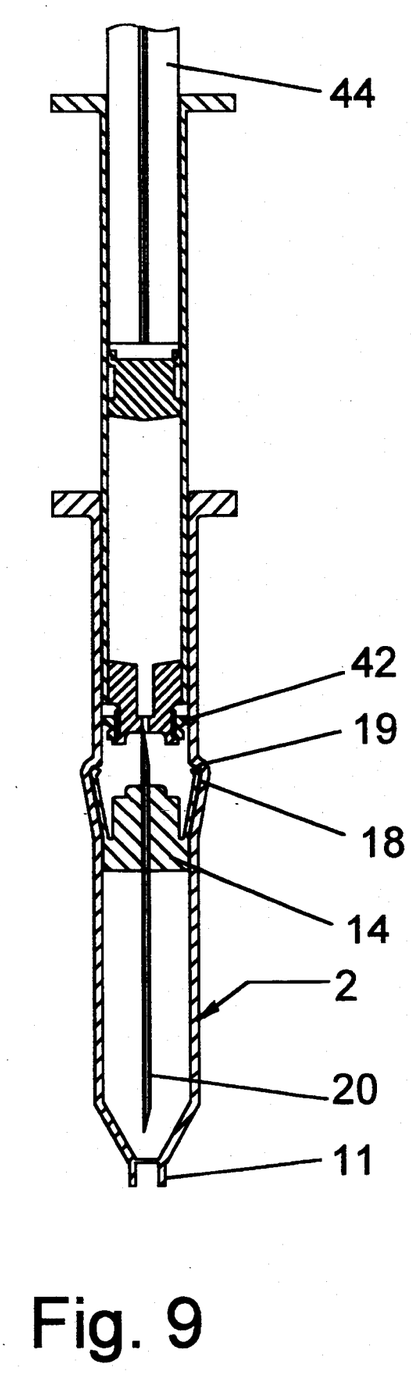
FIG. 9 is a longitudinal cross-sectional view of the syringe of FIG. 8 showing the inner tube being retracted from within the outer tube.

FIG. 3 shows the inner tube 28 of FIG. 2 slidable mounted within outer tube 2 of FIG. 1. The same components have been given the same reference numbers in all the drawings. Gasket 34 is shown at the closed end of inner tube 28 after it was projected toward the closed end by plunger member 44. Plunger member 44 comprises a tubular member 46 terminating with a flat plate 48 which is shown in contact with gasket 34. The upper segment 50 of plunger member 44 is shown slightly larger in cross-section than the remaining portion of tube 46 so that said segment acts as a limiting means for preventing the tube from being pushed too far into inner tube 28. As shown in FIG. 4, when plunger member 44 is fully projected into inner tube 28, it advances gasket 32 to contact needle 20 whereupon the tip 23 of needle 20 punctures area 40 in gasket 32. FIG. 5 shows inner tube 28 projected into outer tube 2 so that gasket 32 makes contact with gasket 14 of outer tube 2. Lock ring 42 is shown at the top of groove 38 and has a groove 52 that is properly aligned so that when gasket 32 pushes gasket 14 forward, ribs 18 will be forced inwardly and the upper flanges 54 of ribs 18 will seat in groove 52 as shown in FIG. 6. As the inner tube 28 is further projected into outer tube 2, the tip 23 of needle 20 punctures the closed area 12 of tube 2 as shown in FIG. 7. As further shown in FIGS. 6 and 7, ribs 18 are locked in groove 52 of lock ring 42. The syringe 1 shown in FIG. 7 is now ready for use. To extract a fluid from a person, needle 20 is inserted into a particular body organ and plunger member 44 is withdrawn as shown in FIG. 8. Plate 48 of plunger member 44 is locked into gasket 34 by any conventional technique such as by bayonet type mount means or means in which the plunger member is inserted and then twisted to lock it in place. With the withdrawal of plunger member 44, a negative pressure is created in space 56 of inner tube 28. This will provide a suction on the tip 22 of needle 20 to withdraw the fluid through needle 20 into space 56. Upon completion, the inner tube 28 is withdrawn so that lock ring 42 slides to the lower end of groove 38 and pulls gasket 14 along with it. This effectively returns needle 20 to within outer tube 2 as shown in FIG. 9. As also shown in FIG. 9, gasket 14 is once more locked into place as ribs 18 expand into groove 19 of outer tube 2. This secures needle 20 within outer tube 2. Plunger member 44 can be removed and then inner tube 28 can be removed with its fluid contents whereupon inner tube 28 can function as the container for the fluid.

Figure 10:
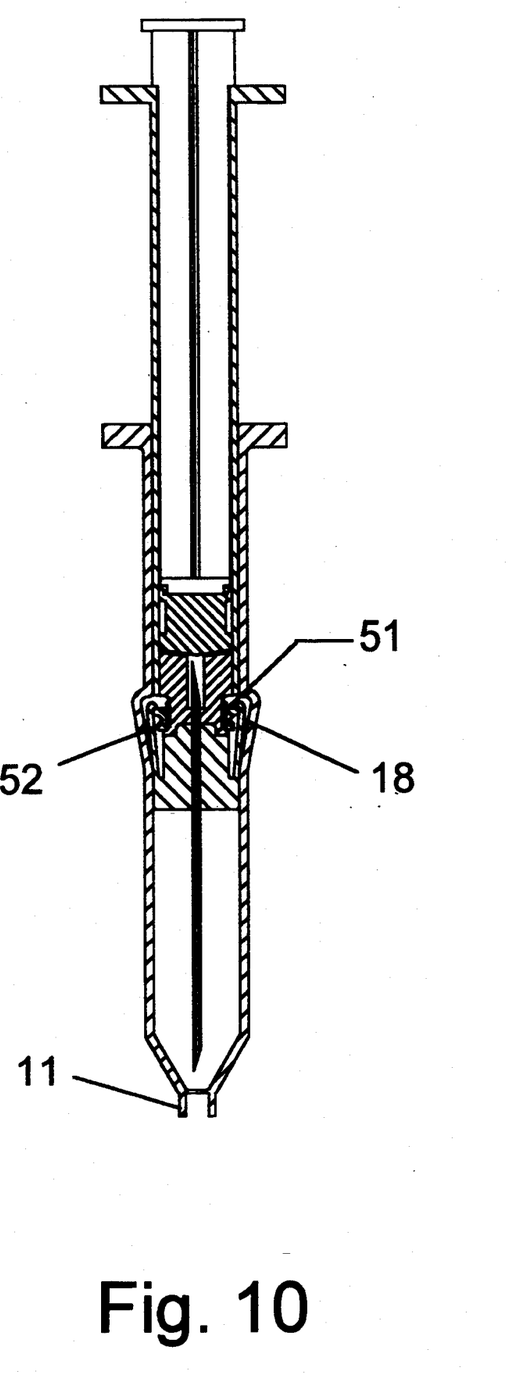
FIG. 10 is a longitudinal cross-sectional view of the syringe of FIG. 9 showing the inner tube being advanced within the outer tube in which the needle/gasket is secured within the outer tube.

After a single use of the syringe 1 as shown in FIG. 9, lock ring 42 is positioned at the lower portion of groove 38 of gasket 32. In attempting to use the syringe again, inner tube 28 would be advanced as shown in FIG. 10 whereupon ribs 18 would not lock into groove 52 of lock ring 42 but instead would press against the upper flange 51 defining groove 52. This will prevent gasket 14 from further advancing in outer tube 2 since the outer diameter of ribs 18 would be larger than the inner diameter of outer tube 2. Thus, as shown in FIG. 10, the needle 20 would be secured within outer tube 2 and could not be used again. To advance gasket 14 within outer tube 2, ribs 18 would have to seat within groove 52 of lock ring 42.

Figure 11:
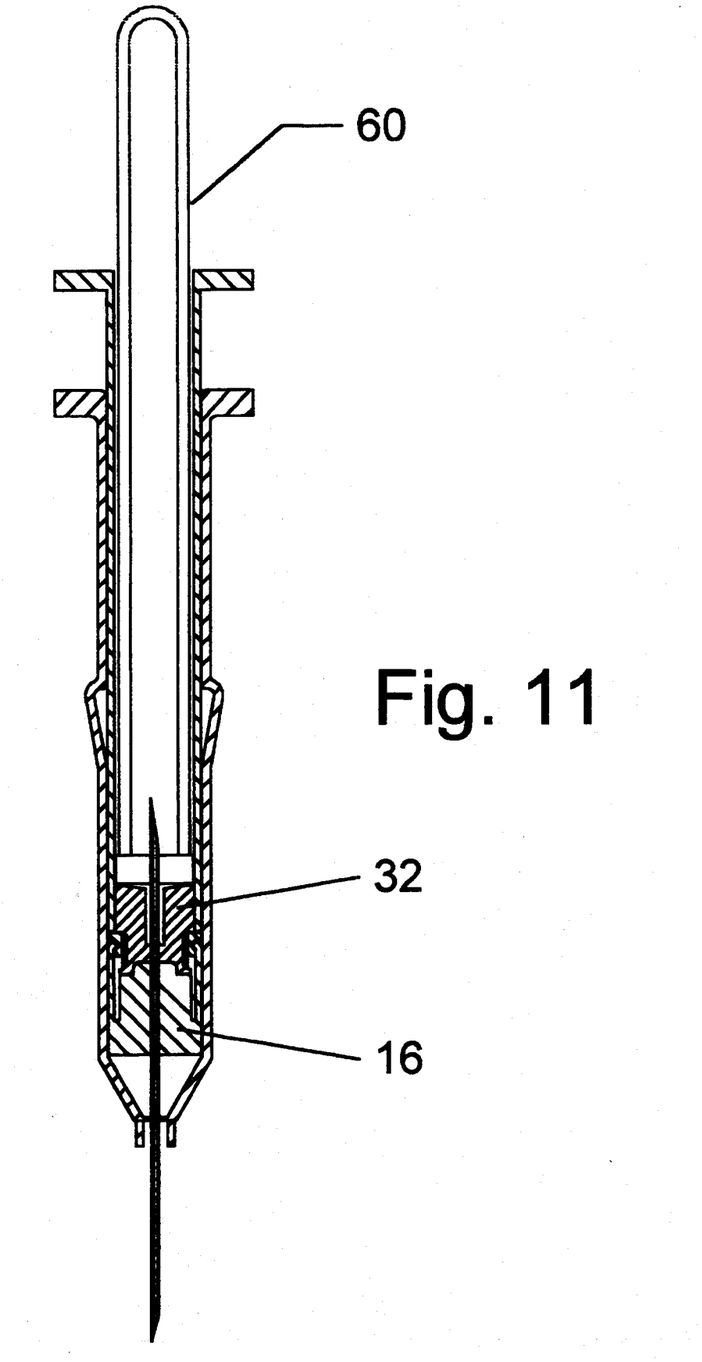
FIG. 11 is a longitudinal cross-sectional view of the syringe of the present invention using a replaceable evacuated collection tube so that multiple extractions can be performed.
Figure 12:
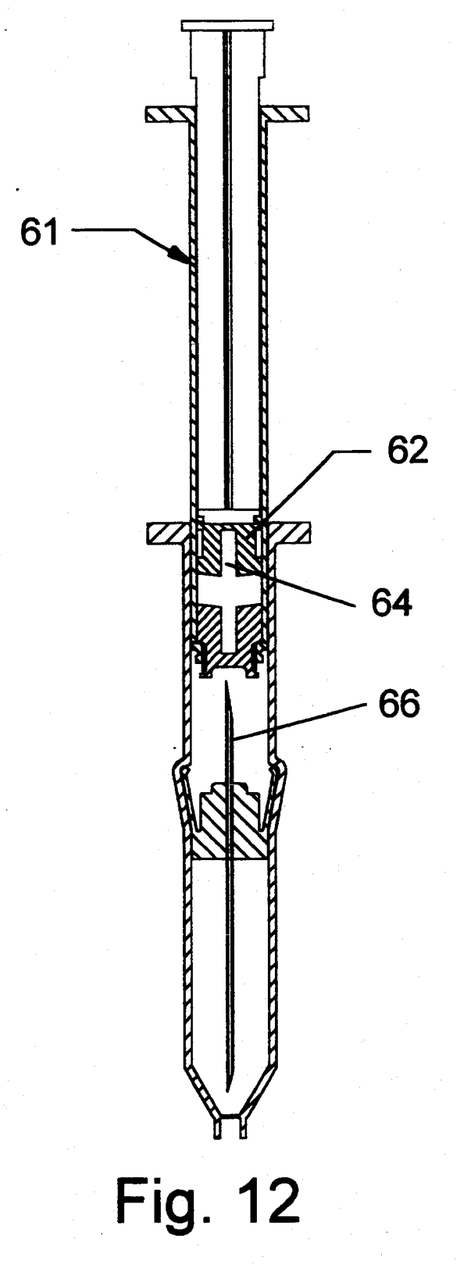
FIG. 12 is a longitudinal cross-sectional view of a syringe of the present invention showing the gasket of an inner tube with a central cavity for accommodating a longer needle so that the syringe can be used as an injector, simple extractor or as a multiple extractor when used in conjunction with an evacuation collection tube.
Figure 13:
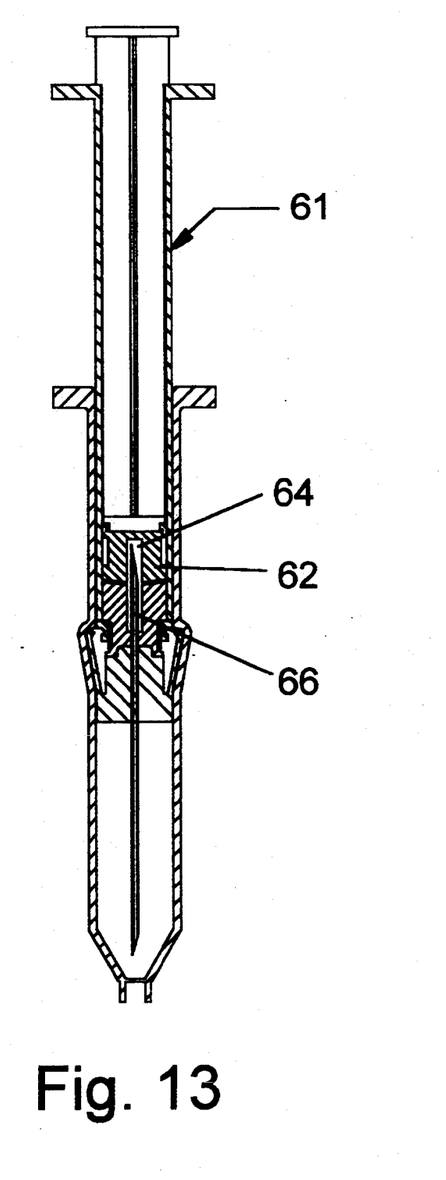
FIG. 13 is a longitudinal cross-sectional view of the syringe of FIG. 12 showing the inner tube abutting the gasket in the outer tube and ready to project the needle out of the syringe.

For multiple use applications, the plunger member 44 is not required but is replaced with an evacuation collection tube 60 as shown in FIG. 11. Once filled, evacuation collection tube 60 would be removed and replaced with a second evacuation collection tube. This could be continued until the necessary number of evacuation collection tubes are filled. FIG. 11 also shows a longer needle 20 at open end 23 which is required to be able to puncture and communicate with the evacuation collection tube. FIGS. 12 and 13 show another embodiment of a syringe 61 in which gasket 62 has an elongated cavity 64 to accommodate a longer needle 66 within syringe 61. Other changes can be made to the various components of the syringe without departing from the scope of the invention which is recited in the following claims.

What is claimed:

1. A syringe with a retractable needle comprising an outer tube having a first end and a second end with said first end being opened; a releasable secured first gasket means within said outer tube and moveable from a secured position to the second end of the outer tube and then back to the secured position, said first gasket means securing a needle opened at both ends and protruding from one end of said first gasket means towards the first end of the outer tube and protruding from the opposite end of said gasket means toward the second end of said first gasket means; an inner tube slidably mounted within said outer tube and having a first end and a second end with a second gasket means secured to the first end of the inner tube and said second gasket means can be secured to and release the first gasket means upon contact with and movement of the second gasket means so that said first gasket means can be projected toward the second end of the outer tube whereupon said needle can be extended outside the outer tube and when said second gasket means is retracted it will return the first gasket means to its secured position within said outer tube; said second gasket means being aligned with the protruding needle from the first gasket means so that said needle is positioned to extend into the inner tube through said second gasket means prior to said second gasket means advancing the first gasket means to the second end of the outer tube; plunger means positioned within said inner tube having a third gasket means at one end so that when the plunger means is retracted from within said inner tube, the third gasket means will provide a sucking force within said inner tube.

2. The syringe of claim 1 wherein the second end of the outer tube is closed by a closure means.

3. The syringe of claim 2 wherein the closure means for the inner tube and the material of the gasket means facing the needle can be punctured by said needle.

4. The syringe of claim 3 wherein the second gasket means has a cavity to accommodate one end of the needle.

5. The syringe of claim 1 wherein the second end of the outer tube has an extended flange to provide a recess at said second end.

6. The syringe of claim 1 wherein said second gasket means has a closure for the inner tube.

7. The syringe of claim 6 wherein said first gasket means has at least one outward extending rib that seats within a groove formed in the wall of the outer tube and wherein the second gasket means of the inner tube has a groove in its outer surface and a lock ring is disposed in said groove and said lock ring can receive said at least one rib of the second gasket means so that upon advancement of said second gasket means within said outer tube, said first gasket means will be advanced to extend the needle outside the outer tube.

8. The syringe of claim 7 wherein said lock ring is out of alignment with said at least one rib when the first gasket means is retracted from the second end of the outer tube so that upon retraction of the first gasket means within said outer tube, the first gasket means will be prevented from advancing the needle outside the outer tube.

9. The syringe of claim 8 wherein the plunger means can be removed from the inner tube and said inner tube can be removed from the outer tube so that said inner tube can be used as a container.

10. The syringe of claim 1 wherein said first gasket means has at least one outward extending rib that seats within a groove formed in the wall of the outer tube.

11. The syringe of claim 10 wherein the second gasket means of the inner tube has a groove in its outer surface and a lock ring is disposed in said groove and said lock ring receives said at least one rib of the first gasket means so that upon advancement of said second gasket means within said outer tube, said first gasket means will be advanced to extend the needle outside the outer tube.

12. The syringe of claim 11 wherein said lock ring is out of alignment with said at least one rib when the first gasket means is retracted from the second end of the outer tube so that upon retraction of the first gasket means within said outer tube the first gasket means will be prevented from advancing the needle outside the outer tube.

13. The syringe of claim 1 wherein the plunger means can be removed from the inner tube and said inner tube can be removed from the outer tube so that said inner tube can be used as a container.

14. A syringe with a retractable needle comprising an outer tube having a first end and a second end with said first end being opened; a releasable secured first gasket means within said outer tube and moveable from a secured position to the second end of the outer tube and then back to the secured position, said first gasket means securing a needle opened at both ends and protruding from one end of said first gasket means towards the first end of the outer tube and protruding from the opposite end of said gasket means toward the second end of said first gasket means; an inner tube slidably mounted within said outer tube and having a first open end and a second end with a second gasket means secured to the first end of the inner tube and said second gasket means can be secured to and release the first gasket means upon contact with and movement of the second gasket means so that said first gasket means can be projected toward the second end of the outer tube whereupon said needle can be extended outside the outer tube and when said second gasket means is retracted it will return the first gasket means to its secured position within said outer tube; and wherein said second gasket means being aligned with the protruding needle from the first gasket means so that said needle is positioned to extend into the inner tube through said second gasket means prior to said second gasket means advancing the first gasket means to the second end of the outer tube.

15. The syringe of claim 14 wherein the second end of the outer tube is closed with closure means at said second end which can be punctured by said needle and wherein said second gasket means provides a closure for the inner tube and the material of the second gasket means facing the needle can be punctured by said needle.

16. The syringe of claim 15 wherein said first gasket means has at least one outward extending rib that seats within a groove formed in the wall of the outer tube.

17. The syringe of claim 16 wherein the second gasket means of the inner tube has a groove in its outer surface and a lock ring is disposed in said groove and said lock ring can receive said at least one rib of the first gasket means so that upon advancement of said second gasket means within said outer tube, said first gasket means will be advanced to extend the needle outside the outer tube.

18. The syringe of claim 17 wherein said lock ring is out of alignment with said at least one rib when the first gasket means is retracted from the second end of the outer tube so that upon retraction of the first gasket means within said outer tube, the first gasket means will be prevented from advancing the needle outside the outer tube.

19. The syringe of claim 14 wherein an evacuation collection tube is positioned within said inner tube and said evacuation collection tube can receive the end of the needle projected through the second gasket means.

* * * * *